United States Patent
Berg et al.

(10) Patent No.: US 7,240,765 B2
(45) Date of Patent: Jul. 10, 2007

(54) CUSTOMIZED HEARING PROTECTION EARPLUG WITH AN ACOUSTIC FILTER AND METHOD FOR MANUFACTURING THE SAME

(75) Inventors: Christian Berg, Uerikon (CH); Hilmar Meier, Zurich (CH)

(73) Assignee: Phonak AG, Staefa (CH)

( * ) Notice: Subject to any disclaimer, the term of this patent is extended or adjusted under 35 U.S.C. 154(b) by 371 days.

(21) Appl. No.: 10/925,136

(22) Filed: Aug. 25, 2004

(65) Prior Publication Data

US 2006/0042865 A1   Mar. 2, 2006

(51) Int. Cl.
*H04R 25/02* (2006.01)

(52) U.S. Cl. .................. 181/135; 181/129; 181/131

(58) Field of Classification Search ............. 181/130, 181/135; 128/864, 865, 868; 381/322, 328, 381/329
See application file for complete search history.

(56) References Cited

U.S. PATENT DOCUMENTS

| | | | | |
|---|---|---|---|---|
| 4,349,083 | A * | 9/1982 | Bennett | 181/135 |
| 6,148,821 | A * | 11/2000 | Falco | 128/864 |
| 6,359,993 | B2 * | 3/2002 | Brimhall | 381/328 |
| 6,533,062 | B1 | 3/2003 | Widmer et al. | |
| 6,766,878 | B2 | 7/2004 | Widmer et al. | |
| 2003/0112990 | A1 | 6/2003 | McIntosh et al. | |
| 2003/0133583 | A1 | 7/2003 | Widmer et al. | |
| 2005/0247715 | A1 * | 11/2005 | Berg | 181/135 |
| 2006/0023908 | A1 * | 2/2006 | Perkins et al. | 381/328 |

FOREIGN PATENT DOCUMENTS

| | | |
|---|---|---|
| EP | 0336487 A1 | 10/1989 |
| EP | 0590698 A2 | 4/1994 |
| EP | 1039779 A2 | 9/2000 |
| EP | 1046382 A1 | 10/2000 |
| WO | WO 96/40479 | 12/1996 |
| WO | WO 01/76520 A1 | 10/2001 |
| WO | WO 02/24127 A2 | 3/2002 |

OTHER PUBLICATIONS

European Search Report dated Dec. 28, 2004 for application No. 04020175.8.

* cited by examiner

*Primary Examiner*—Brian Sircus
*Assistant Examiner*—Terrence R. Willoughby
(74) *Attorney, Agent, or Firm*—David S. Safran

(57) ABSTRACT

The invention relates to a hearing protection earplug, comprising a hard shell (10) having an elasticity of from shore D 85 to shore D 65 and having an outer surface individually shaped according to the measured inner shape of the user's outer ear and ear canal for being worn at least in part in the user's ear canal, the shell comprising a filter cavity (12) having at least one orifice (20, 30, 40) into which a passive acoustic filter element (21, 31) is inserted for forming, together with said orifice, a passive acoustic filter. The invention also relates to a use of such an earplug and a method for manufacturing such an earplug.

12 Claims, 3 Drawing Sheets

CUSTOMIZED HEARING PROTECTION EARPLUG WITH AN ACOUSTIC FILTER AND METHOD FOR MANUFACTURING THE SAME

BACKGROUND OF THE INVENTION

1. Field of the Invention

This invention relates to a customized passive hearing protection earplug and to a method for manufacturing the same.

2. Description of Related Art

A large part of the population is exposed to hazardous noise from time to time. This can be at work, whilst traveling, during leisure activities or at home. The exposure can lead to permanent hearing loss, distract people's attention from other hazards or simply cause stress. In order to prevent both accidents and permanent hearing damage, hearing protection devices (HPDs) have been provided in many styles and over many years. It started with the earmuff which is still very relevant and addresses very noisy environments (e.g. airports, construction, shooting) or complex working/communication situations (e.g. fighter pilots). Over the years development of biocompatible soft materials has enabled soft earplugs in different styles and colors as well as recent development of "one fits many" standard semi-soft earplugs in silicon-rubber type materials. For severe situations even the combination of an earmuff and an "in-the-ear" HPD is required to achieve desired attenuation. The physical limitation of hearing protection based on ear worn devices is defined where bone-conduction (body acoustics) becomes dominant at around 40 dB attenuation.

A common disadvantage of the above mentioned HPD styles is wearing discomfort. In case of the earmuffs, they are large which creates difficulties in combination with other head worn gear and they "close off" the ear too much for most applications. The in-the-ear styles mentioned are devices made to fit "the average" ear in one way or the other. Either the fit is provided by softness of the material which leads to undefined device insertion and undefined attenuation, or the fit is provided by standard shaped structures intended to block off the ear canal. In both cases the flat distribution of the individual shape of the outer ear and the ear canal leads to bad fit, pressure points in the ear and undefined positioning of the device.

To address this wearing comfort issue, in-the-ear hearing aid technology has been applied making customized ear molds with passive acoustical filter. These are long lasting devices with good wearing comfort. However, this customization process is traditionally a very manual process creating varying results over time, low reproducibility and the quality is very operator skill dependent.

The idea to use rapid prototyping technology, such as layer-by-layer laser sintering, in manufacturing shells, primarily for hearing aids, is described, for example, in U.S. Pat. No. 6,533,062 B1 or US 2003/0133583 A1.

HPDs are often passive (i.e. not powered) and some simply amount to a plug in the ear; while more sophisticated (but still passive) HPDs may include acoustic chambers and filters, for passing or attenuating selected frequencies.

Different in-ear devices are presently used in a wide range of human activities. From the performance standpoint, in particular with respect to comfort, HPDs, like hearing aids, really have to be custom-fitted to an individual's ear shape. In-ear devices are inserted into the outer part of an individual's ear canal and, depending on the size of the in-ear device, may as well occupy parts of an individual's concha, also called pinna.

Often, in-ear HPDs or earplugs of some standard size and a certain damping characteristic are used to cover hearing protection needs of a wide variety of different ear anatomies. For a certain individual, a prediction of the performance of such an earplug is difficult and it is not possible to adapt the earplug's filter characteristic to specific needs of an individual. However, in many cases customized passive HPDs that provide a predictable attenuation of acoustic energies across the audible frequency range are desired. With conventional shell making technology, this has been prepared in form of a more or less sophisticated filter module component. This component is mounted in or on the shell faceplate and provides a defined acoustic "gate" through the HPD. Supply of such filters is rather limited, prices are high and the flexibility in application is not convincing.

U.S. Pat. No. 6,148,821 discloses a selective non-linear attenuating soft earplug which is a passive in-the-ear (ITE) device. A filter tube is inserted into the shell, and the hollow interior of the filter tube may be set into communication with the surroundings by rotating it. A sound attenuating filter is inserted into the distal end portion of the tube. When the filter whose attenuating characteristics cannot be modified, is to be changed against another filter, the tube must be removed from the earplug, and the filter must be replaced. The tube is then to be reinserted into its receiving cavity of the HPD.

Another type of filter is described in the published U.S. patent application no. 2003/0112990; this document is directed to an expandable in-ear device. The filter may be a band-pass filter; it has the shape of a little rectangular block to be inserted into a square-sectioned opening of the earplug from which it slightly protrudes to the exterior. The filter is removably locked to a handle of the HPD that is in turn secured, preferably glued, to the earplug platform. Thus, the filter can normally not be removed from the HPD.

Customized earplugs having a shell with an outer shape corresponding individually to the measured inner shape of the user's outer ear and ear canal which are produced e.g. by layer-by-layer laser sintering from a powder material are described for example in U.S. Pat. No. 6,533,062 B1.

The increasing demand for fully customized HPDs will require flexible devices that are individually fitted regarding both the anatomy and the acoustics of the wearer's ear. For evident reasons, short delivery times and low costs will be determining for a widespread use of new HPDs.

Known prefabricated filter assemblies as such described above are either complicated to handle or, although allowing short delivery, remain expensive.

It is an object of the present invention to provide for a customized hearing protection earplug which allows for an individual and flexible sound attenuation function and which is easy to manufacture. It is a further object to provide for a corresponding manufacturing method.

SUMMARY OF THE INVENTION

This object is achieved by a hearing protection earplug as defined in claim 1 and by a manufacturing method as defined in claim 16. The invention is beneficial in that, by providing the shell with a filter cavity having at least one orifice into which a passive acoustic filter element is inserted for forming, together with said orifice, a passive acoustic filter, a semi-integration of the acoustic filter function into the shell is achieved so that, although a standard filter element may be used, an individually optimized acoustic filter function may be achieved by individually shaping and sizing the filter cavity, i.e. the orifice receiving the filter element, which forms the "tube part" of the filter, in order to achieve the desired attenuation function.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIG. 1 shows a perspective view of a passive hearing protection earplug. The earplug comprises a shell 10, which nipple comprises a distal portion 11 insertable into an user's ear-canal and an outer portion 13 for contacting the user's outer ear. When the earplug is worn by user, the outer portion 13 protrudes from the user's ear-canal.

Basically, earplugs can be divided into four types, the so called completely-in-canal earplug, the mini-canal earplug, the half-shell earplug, and the full-shell earplug. The full-shell type earplug is the largest earplug type and the outer portion 13 would cover large parts of the earlap. For a full-shell type earplug, the outer portion 13 would have a more complex shape according to the individual's ear's shape. A completely-in-canal type earplug is the smallest earplug type and is hardly visible when worn by the user. For a completely-in-canal type earplug, the outer portion 13 essentially would have the shape of an ellipsis or circle.

Figure 1:
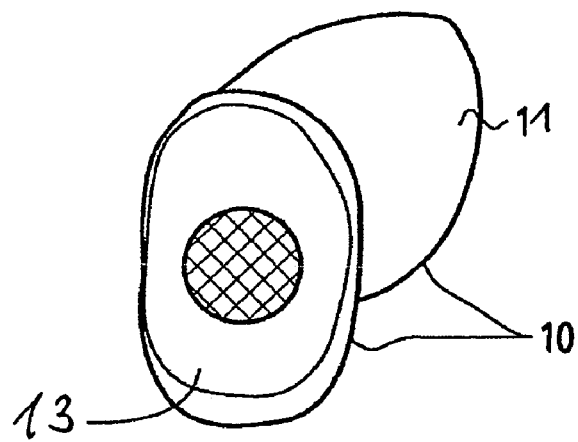
FIG. 1 is a perspective view of a hearing protection earplug according to the invention.
Figure 2:
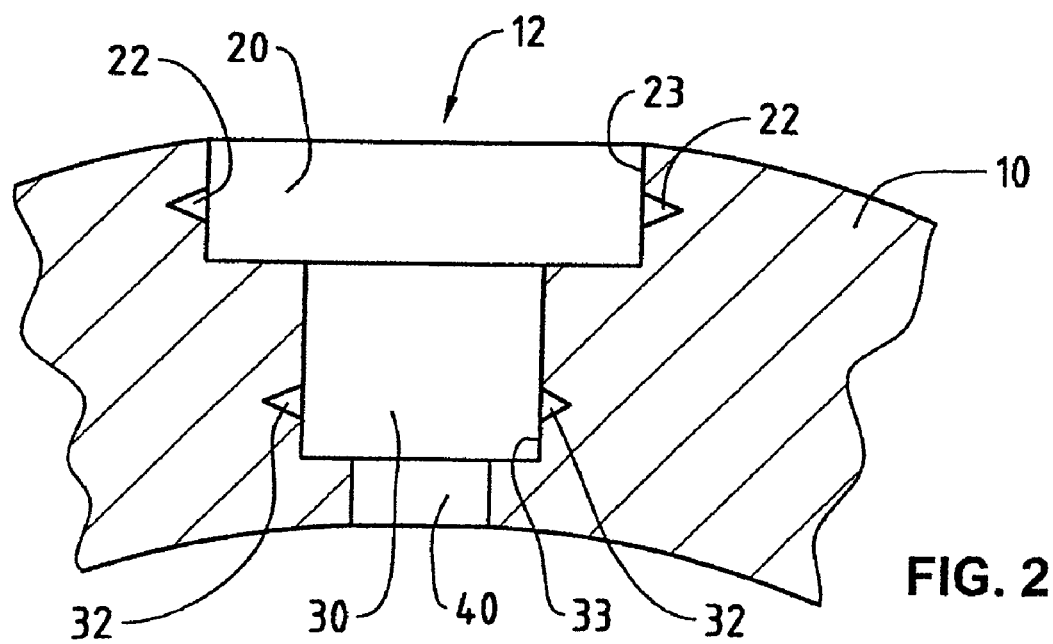
FIG. 2 is a longitudinal sectional view of the faceplate of the earplug of FIG. 1 comprising a filter cavity for filter elements on an enlarged scale.

The distal end of the shell 10 forms a faceplate and comprises a through-hole or filter cavity 12 which comprises orifices of different sizes. As an example, in FIG. 2 three orifices 20, 30, and 40 are shown. However, the invention relates to any number of orifices. The orifices may have any suitable shape. As an example, in FIG. 2 orifices of a cylindrical shape are shown. Orifices may be ordered, for example, with respect to their diameters as shown in FIG. 2. However, orifices may also be arranged in any order. Ordering of orifices as shown in FIG. 2 may have advantages for the installation of passive acoustic filters as will be described below. In the practice of the invention the orifices may have shapes and sizes different to those shown in the drawings. In some cases it is preferred to implement cylindrical orifices. Exponential and other complex functions are also possible, which, however, in some cases might be difficult to be controlled and dimensioned.

Figure 3:
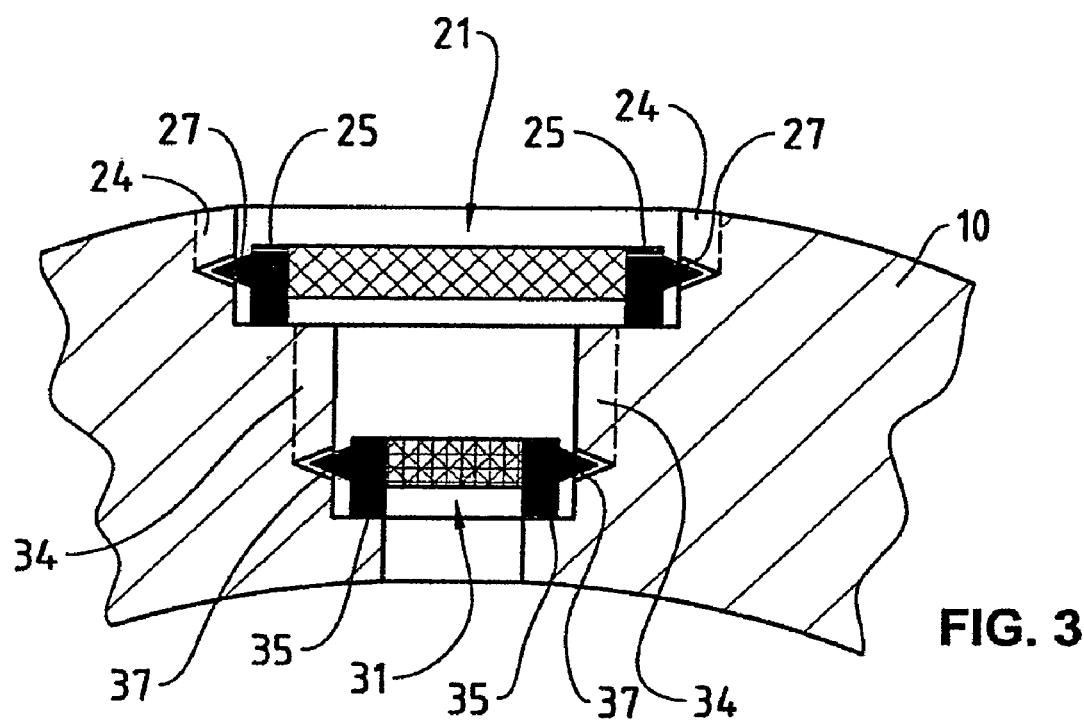
FIG. 3 is a view like FIG. 2, with passive acoustic filter elements having been inserted in the filter cavity.

FIG. 3 shows the same view as that of FIG. 2, but with passive acoustic filter elements 21 and 31 inserted into the orifices 20 and 30. For the fixation of the acoustic filter elements 21, 31 in the orifices 20, 30, any suitable technique can be applied. In FIG. 3, for example, circular grooves 22 and 32 in the vertical walls 23 and 33 of the orifices 20 and 30 are shown. The walls 23 and 33 further comprise a pair of cylindrical recesses 24 in the upper wall 23 and another pair of cylindrical recesses 34 in the lower wall 33. These recesses are shown in dotted lines in FIG. 3. Each recess 24, 34 extends, for example, over about 90° of the circumference of the corresponding wall, each wall portion 23, 33 having two cylindrical recesses equally spaced over the circumference. These recesses serve for the insertion of the passive acoustic filters 21 and 31. One of them, for example the passive acoustic filter 21, is represented as a top view in FIG. 4.

Figure 4:
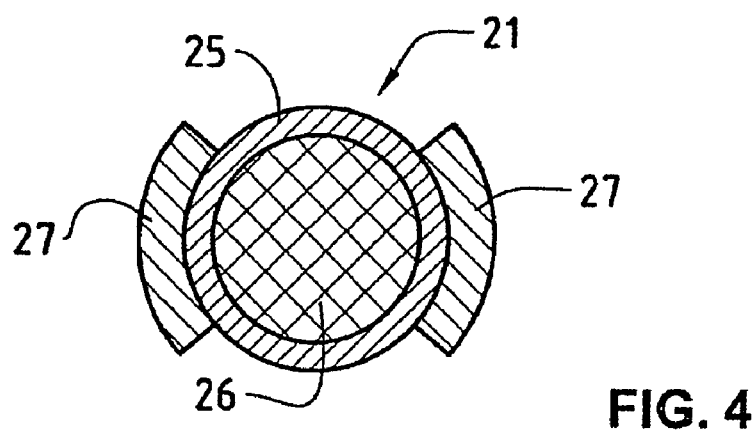
FIG. 4 is a top view of a passive acoustic filter element to be inserted in the filter cavity of FIGS. 2 and 3.

The passive acoustic filter 21, see also FIG. 4, can have e.g. a mainly cylindrical filter body 25 made from an appropriate material such as a resistant synthetic resin that can be preferably bio-compatible and/or sterilizable. The filter body 25 is hollow and contains a filter component 26, the structure and nature of which provide for defined filter characteristics. Basically, the filter characteristics of the filter element 26 is determined by the used structure and the used material. For example, the filter component 26 may consist of a membrane of a defined thickness and material. Such a membrane leads basically to a high-pass characteristic of the filter component 26. By choosing appropriate filter components for the acoustic filter elements 21 and 31, advanced acoustic filters can be constructed. It may also be possible to have the user adapt the acoustic filters 21 and/or 31 to particular conditions; for this purpose, the acoustic filters 21 and/or 31 may be removable.

The upper and lower horizontal bordering surfaces of the passive acoustic filters 21, 31 may be sound transparent in a manner known per se. For example, the passive acoustic filter bodies 25, 35 may have the general shape of cylinders. Thickness and/or diameter of the passive acoustic filter elements 21, 31, and therefore of the filter bodies 25, 35, may vary according to the desired attenuation or frequency response.

A pair of projections 27, 37 is attached to the bodies 25, 35 of the passive acoustic filter elements 21, 31, with the projections 27, 37 being shaped to fit within the mating grooves 22, 32.

The insertion of the passive acoustic filter elements 21, 31 into the orifices 20, 30 is simple. The passive acoustic filter 31 is inserted first. The filter body 35 is introduced from above into the orifice 30 and rotated until the two pairs of projections 36 are aligned with the corresponding recesses 34 respectively, and the passive acoustic filter now falls home into the orifice 30. The filter body 35 is now turned by about 90° so that the projections 36 remain captioned within the grooves 33. The insertion of the passive acoustic filter 21 is done accordingly.

Suitable means (not shown) may be provided to retain the passive acoustic filters 21, 31 in their inserted position. For example, the grooves 22, 32 may have a depth that diminishes in the regions where the projections 27, 37 should be blocked, or the projections may be shaped in an appropriate manner to be clamped in the grooves; this possibility is indicated in FIG. 3 where the outer generally circular contour of the projections 27 is slightly eccentrically shaped.

The passive acoustic filters 21, 31 may be removed from the orifices 20, 30 by executing the above-indicated steps in the reverse manner.

The described arrangement of orifices 20, 30, 40 and passive acoustic filter elements 21, 32 act together to form a passive acoustic filter. Since part of the filter function or characteristics is determined by the shape and size of the filter cavity 12, i.e. of the orifices 20, 30, 40, (i.e. the orifices 20, 30, 40 provided for the "tube part" of the filter), the filter may be considered as a semi-integrated filter. In particular, the shell 10, i.e. the orifices 20, 30, 40, does not only serve to fix the filter elements 21, 31 but also serves to "tune" the filter by the selected shape and size of the orifices 20, 30, 40 and the selection of the points where the filter elements 21, 31 are located within the orifices 20, 30, 40. In general, main parameters for adjusting the filter characteristics of the semi-integrated passive filter may be the number of orifices, sizes of orifices, as well as sizes and material of the passive acoustic filters. These parameters are determined when the earplug is manufactured, for example according to an acoustic model of the user's ear-canal with inserted earplug.

Generally, the shell 10 is a customized hard shell having an elasticity from shore D 85 to shore D 65, for example made of polyamide, and an outer surface individually shaped according to the measured inner shape of the user's outer ear and ear canal. The customized shell may be produced by an additive or incremental build-up process, such as layer-by-layer laser sintering (also known as "selective laser sintering") of a powder material. The inner shape of the user's outer ear and ear canal may be measured, for example, by three dimensional (3D) laser scanning of the ear or by taking an impression of the ear which then undergoes 3D laser scanning. Such manufacturing processes are described for example in U.S. Pat. No. 6,533,062 B1.

Preferably, the shape and/or the axial length of orifices 20, 30, 40 and/or the position at which the passive acoustic filter elements 21, 31 are fixed within the respective orifices 20, 30 is individually selected according to a desired acoustic filter function of the filter elements 21, 31 acoustically cooperating with the orifices 20, 30, 40. According to a preferred embodiment, these parameters are individually determined according to the measured inner shape of the user's outer ear and ear canal for individually optimizing the desired filter function. By an appropriate selection of these parameters of the filter cavity 12, i.e. of the shell 10, an individual filter function may be achieved even when using low-price standard filter elements 21, 31.

After having been manufactured, the geometry of the orifices cannot be changed easily anymore. However, according to the procedure described above, passive acoustic filter elements 21, 31 may be easily exchanged. Therefore, for example, when the wearer of the earplug wants to adapt the HPD to a certain acoustic environment, different acoustic damping needs can simply be realized to some extent by an appropriate exchange of passive acoustic filter elements 21, 31.

The simple exchange of the passive acoustic filter elements 21, 31 also provides ease of service of the earplug, for example a cleaning of the shell 10 and replacement of the passive acoustic filter elements 21, 31 after exposure to a dirty environment. Further, it is possible to define a standard set of passive acoustic filters 21, 31 and use parameters of the orifices for a proper design of the semi-integrated passive filter. A standard set of passive acoustic filters will lead to lower manufacturing costs and lower service costs as well.

The outer horizontal surface of the passive acoustic filter elements 21, 31 may be provided with means for an easier seizing of the filter element in order to insert or to remove it. Instead of one pair of angularly spaced projections 27, 37, it is possible to provide three, four or even more projections that have of course a smaller angular extension, etc. Several filter structures as shown in FIG. 3 may be arranged in the same HPD, for example as parallel filter structures. Such a parallel filter structures may be designed to be active simultaneously leading to a desired overall filter characteristic of the HPD. Parallel filter structures may also be designed to be switchable, for example be means of a circular and turnable faceplate 11, whereas a defined number of filter structures can be activated or deactivated by turning the faceplate 11 appropriately.

In FIGS. 1 to 4 the filter cavity 12 of the shell 10 is shown as part of a faceplate at the proximal (outer) end of the shell 10. However, alternatively, the filter cavity 12 may be provided in a distal wall or in a intermediate wall of the shell 10.

Figure 5:
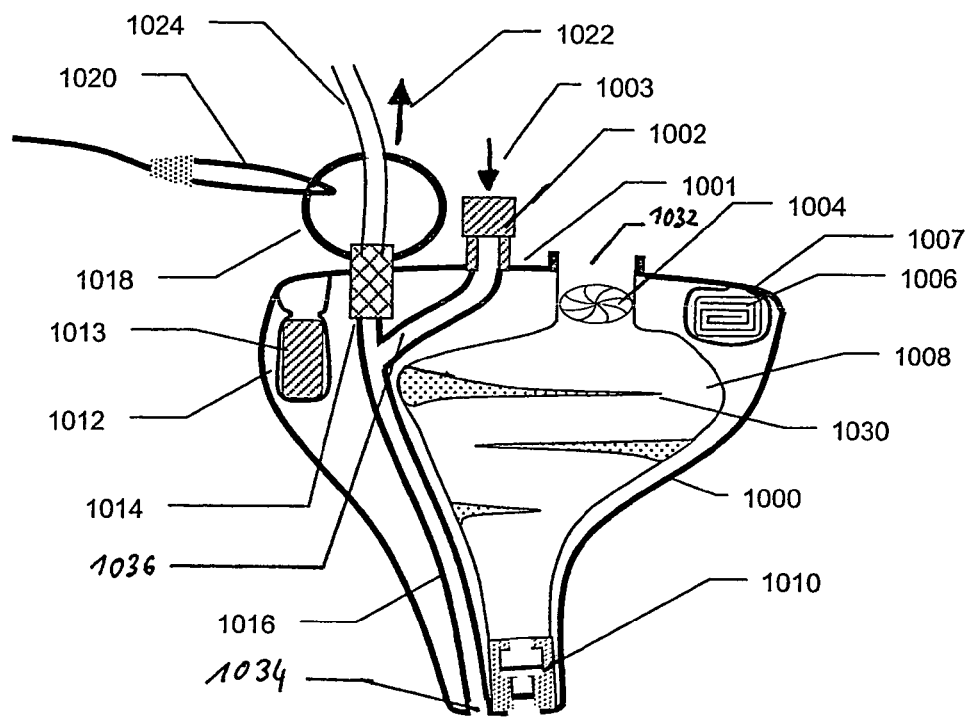
FIG. 5 is a longitudinal sectional view of a further embodiment of a hearing protection earplug according to the invention.

An example in which the filter cavity is provided in a distal wall of the shell is illustrated in FIG. 5 which shows an example of a customized passive hearing protection earplug with a customized hard shell 1000 having a faceplate 1001 as its outer end with a sound input opening 1032 which is acoustically connected with a resonance cavity 1008. An semi-integrated acoustic attenuation filter 1010 is provided at the inner (i.e. distal) end of the resonance cavity 1008 which extends from the sound input opening 1032 at the faceplate 1001 to the filter 1010. The filter 1010 may have a construction similar to that illustrated in FIGS. 2 and 3.

FIG. 5 shows an example of a passive hearing protection earplug, wherein some additional features are combined which may be advantageously implemented by manufacturing the shell of the earplug by an additive build-up process, such as layer-by-layer laser sintering.

The sound input opening 1032 is provided with a mechanical peak clipper 1004, a multi-purpose cord adapter element 1014 with an in-situ measuring hole for optionally connecting the measuring hole to an external measuring tube 1024 or to a plug for closing the measuring hole in the normal operation of the earplug, and a sound inlet opening which is provided with a button 1002 which is manually operable in the direction 1003 to act as an attenuation button closing the sound inlet opening or as communication button opening the sound inlet opening for sound input into a sound passage 1036 which merges at its distal end with an in-situ measuring channel or tube 1016 which is acoustically connected to the measuring hole in adapter element 1014 and which extends to an inner sound opening 1034 at the inner end of the shell 1000. The resonance cavity 1008 is provided with an inner mechanical structure 1030 for frequency tuning. The tubes 1036 and 1016 are formed integral with the shell 1000. Further, also an insert cavity 1007 for a RFID (radio frequency identification device)-tag 1006 and an insert cavity 1012 for a detectable metal part 1013 are formed integral with the shell 1000. At the adapter element 1014 or at the plug for closing the measuring hole of the adapter element a cord fixation ring 1018 may be provided for fixing a neck cord 1020 at the shell 1000 for preventing loss of the earplug. The ring 1018 or the cord 1020 also may serve to manually pull the earplug in the axial direction 1022.

In the following, these additional features and their functions will be explained in more detail.

Multipurpose Cord Adapter

In order to confirm acoustical performance of an HPD, an in-situ measurement tube is implemented to allow measurement of attenuation when the individual wears the device. Naturally this tube needs to be closed off during normal operation. The core element of this tube is the faceplate component referred to a multipurpose cord adapter 1014 that embodies several functions and features: fixation of external in-situ measurement probe tube 1024, one possible holder of the cord fixation ring 1018 for the neck cord 1020, holder of an ergonomic pull means (e.g. the cord fixation ring 1018,)

for an inverse anatomy switch, holder of a plug for closing the in-situ tube during normal operation. If the element is made of metal it can serve as a metal component for detection purposes 1013 which in that case spares an extra insert cavity 1012. The design of the multipurpose cord adapter element 1014 is given extensive freedom (shape, material, insertion/removal concept, etc.) due to the base technology used for the faceplate portion of the earplug 1001.

Communication/Attenuation Button

A core function of a passive HPD is to enable temporary audio bypass for purposes like listening to speech, alarm or other desired audio signals even though they are mixed with loud noise. This is often performed by a push/return-button opening a tube either bypassing the filter of the system or leading into the in-situ measurement probe tube 1016 on the inside of the closing plug to be connected to the adapter element 1014 when the measuring tube 1024 is removed. The integration of such a device into the faceplate 1001 overcomes many drawbacks of similar standard component solutions (e.g. complex tubing, acoustical leakage). An even more integrated solution is achieved by building the switch directly into the multipurpose cord adapter core element 1014 replacing the sealing plug. If the button is made of metal it could serve as a metal piece for the detection function, thereby eliminating the need for the separate metal part 1013.

Inverse Anatomy Force Button

A further level of integration of the on/off switch is based on the shell technology combined with the natural anatomy of the outer ear. In addition to a defined audio "leak" via a tube 1016 through the HPD, there is the alternative of creating a temporary leak between the device and the outer ear by slightly pulling the device out of the ear. This pull can be done by the cord 1020 or directly by grip and pull on the cord ring 1018. If the shell 1000 is shaped in an appropriate manner, the ear shape is such that the device will be naturally pulled back in place when the pull is relaxed.

Intelligent Passive HPD

Inserting a device into the ear principally blocks the acoustical tube (ear canal) and destroys the natural outer ear amplification and frequency shaping (open ear gain, OEG). The open ear has a natural resonance in the frequency area of the most critical speech information, hence this loss is a real loss and not normally desired. The resonance frequency is given by the length of the tube; hence there is a need for compensation of the reduced length. This can be individually modeled and implemented with a defined acoustical front (outer) chamber 1008 and artificially stretched to a desired length by a mechanical means 1030 for resonance shaping directly integrated into the shell making process, possibly in combination with frequency shaping filter 1010 and means for maximum power limiting such as a mechanical peak clipper 1004.

Mechanical Peak Clipping

Many applications for HPDs experience strong variations in noise exposure over time. The extreme example is people shooting with guns (military, hunters) where speech communication in-between the actions is strongly desired and where the sound gets very loud for a short time. In active devices such conditions have been solved with so-called "peak clippers" which are fairly easy to implement in electronics and which limit the output of the device independent of the input signal while leaving the signal undistorted for normal noise levels. For a passive device this can be realized by a pressure sensitive valve 1004 opening or blocking the audio canal at the sound inlet.

Detectable HPD

HPDs are mostly used in industrial environments. In the food processing industry an additional requirement also affects these devices. Any foreign particle (to the food ingredients) must be detectable within the production process. For HPDs this implies that the devices need to contain a certain amount of metal to enable the detection equipment to find it if lost in the production line. Metal can be inserted into HPDs in a number of different ways: metal can be mixed into the shell base material 1000, a specific metal component 1013 can be mounted in a prepared cavity 1012, the cord adapter faceplate element 1014 can be made of metal and the button part of the on/off switch 1002 can be made of metal. In a HPD with a RFID tag, the tag itself is detectable if the equipment for detection is implemented in the production line.

HPD Wearing Compliance

Wearing of HPDs in industrial environments obliges to regulations in most countries. Assuming that the devices have the desired protective effect when they are worn (most other topics described address this very issue), the wearing itself becomes the compliance control topic. With recent developments in miniaturized RFID (radio frequency identification devices) technology, it becomes feasible to implement such devices into a customized HPD given the shell technology described. The RFID tag 1006 is inserted into a predefined cavity 1007 and when the wearer passes through gateways equipped with RFID detection systems, the positions of the two HPDs can be obtained and the control function carried out according to whether a predefined condition regarding the detected positions is fulfilled or not (e.g. separation of the HPDs according to the width of the head and height of the HPDs according to the ear height). As mentioned, the RFIDs can also serve as HPD detection devices in food production processes.

Basic Functions

Functions that conventionally are mounted components, such as a grip handle for insertion and removal of the HPD, can easily be integrated with use of the shell technology. The product design and assembly more and more becomes a software issue and the individual product is increasingly designed to order according to the specific requirements of each customer.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A hearing protection earplug, comprising a hard shell having an elasticity of from shore D 85 to shore D 65 and having an outer surface individually shaped according to a measured inner shape of a user's outer ear and ear canal for being worn at least in part in said user's ear canal, said shell comprising a filter cavity having at least one orifice into which a passive acoustic filter element is inserted for forming, together with said orifice, a passive acoustic filter; wherein said passive acoustic filter element and said at least one orifice having said filter element inserted therein comprise means for detachably fixing said filter element within said orifice; and wherein said means for detachably fixing said filter element within said at least one orifice are bayonet means adapted to fix said filter element by a combination of a rotary and an axial movement of said filter element relative to said orifice.

2. The earplug according to claim 1, wherein said shell comprises a faceplate at an outer end of said shell, said faceplate comprising said filter cavity.

3. The earplug according to claim 1, wherein said shell comprises a distal wall at an inner end of said shell, said distal wall comprising said filter cavity.

4. The earplug according to claim 1, wherein said shell comprises an intermediate wall located between an outer end and an inner end of said shell, said intermediate wall comprising said filter cavity.

5. The earplug according to claim 1, wherein said filter cavity comprises at least three serially arranged orifices, with at least two of said orifices having inserted a passive acoustic filter element for forming, together with the respective orifice, a passive acoustic filter.

6. The earplug according to claim 5, wherein at least two of said orifices are of different size.

7. The earplug according to claim 1, wherein said filter cavity and said orifices are essentially cylindrically shaped.

8. The earplug according to claim 1, wherein said passive acoustic filter element is a membrane filter element.

9. A hearing protection earplug, comprising a hard shell having an elasticity of from shore D 85 to shore D 65 and having an outer surface individually shaped according to a measured inner shape of a user's outer ear and ear canal for being worn at least in part in said user's ear canal, said shell comprising a filter cavity having at least one orifice into which a passive acoustic filter element is inserted for forming, together with said orifice, a passive acoustic filter; wherein said passive acoustic filter element comprises a filter body to receive a filter component; and wherein said at least one orifice comprises an annular groove in a side wall thereof, and wherein at least two radially protruding, circumferentially spaced apart projections, adapted to engage with said at least one groove, are provided on a circumference of said filter body.

10. The earplug according to claim 9, wherein said projections are partially annularly shaped.

11. The earplug according to claim 9, wherein a wall of said at least one orifice comprises at least two partially annular cylindrical recesses circumferentially spaced apart which are axially connected with said annular groove and which are adapted for insertion of said projections of said passive acoustic filter element order to engage said projections with said annular groove.

12. The earplug according to claim 11, wherein said recesses are equally spaced on a circumference of said wall.

* * * * *